United States Patent [19]
Groenewold et al.

[11] Patent Number: 5,647,841
[45] Date of Patent: Jul. 15, 1997

[54] MOTOR-DRIVEN HAND-HELD MASSAGING DEVICE

[75] Inventors: Vera Groenewold, Griegstr. 14 A, Berlin DE-14193; Michael Schmett, Berlin, both of Germany

[73] Assignee: Vera Groenewold, Berlin, Germany

[21] Appl. No.: 512,896

[22] Filed: Aug. 9, 1995

[30] Foreign Application Priority Data

Feb. 4, 1995 [DE] Germany ............... 195 04 761.3

[51] Int. Cl.$^6$ ................. A46B 13/04; A61H 7/00
[52] U.S. Cl. ............... 601/114; 601/17; 601/18; 601/159; 601/160; 15/29; 401/281
[58] Field of Search ............ 601/17, 18, 112–114, 601/154, 155, 159, 160; 15/29, 24, 28; 401/281; 239/525, 243, 380

[56] References Cited

U.S. PATENT DOCUMENTS

| | | | |
|---|---|---|---|
| 1,342,994 | 6/1920 | Fitzgerald | 601/160 X |
| 1,479,233 | 1/1924 | Gottlieb | 15/29 |
| 2,140,307 | 12/1938 | Belaschk et al. | 15/28 |
| 3,469,470 | 9/1969 | Gaudry | 15/28 X |
| 3,906,574 | 9/1975 | Kaeser | 15/29 |
| 3,910,265 | 10/1975 | Coleman | 601/160 |
| 3,968,789 | 7/1976 | Simoncini | 601/114 X |
| 5,105,802 | 4/1992 | Pokorny | 601/154 X |
| 5,313,682 | 5/1994 | Chamieh | 15/29 |
| 5,385,532 | 1/1995 | Shyu | 601/160 |
| 5,500,972 | 3/1996 | Foster | 15/28 |

FOREIGN PATENT DOCUMENTS

| | | |
|---|---|---|
| GM 7306880 | 6/1973 | Germany . |
| 28 30 480 A1 | 1/1980 | Germany . |
| 8630100 U | 4/1987 | Germany . |
| 9301028 U | 4/1993 | Germany . |
| 43 06 242 A1 | 9/1994 | Germany . |
| 1 480 265 | 10/1974 | Italy . |

*Primary Examiner*—Danton D. DeMille
*Attorney, Agent, or Firm*—McGlew and Tuttle

[57] ABSTRACT

The present invention pertains in general to a motor-driven hand-held massaging device for body massage, with a cosmetic or medical massaging substance optionally fed in and consists of a housing with a grip part, a storage chamber for the massaging substance, and a massaging means. In particular the present invention is an inexpensive motor-driven hand-held massaging device, use of which guarantees a more effective massaging action and convenient handling of massaging substances. The device includes a hand-held massaging device with a plurality of rotating massaging brushes 11 and the massaging substance is able to be fed to the individual massaging brushes 11 at controllable intervals.

18 Claims, 3 Drawing Sheets

MOTOR-DRIVEN HAND-HELD MASSAGING DEVICE

FIELD OF THE INVENTION

The present invention pertains in general to a motor-driven hand-held massaging device for body massage, with a cosmetic or medical massaging substance optionally fed in and consists of a housing with a grip part, a storage chamber for the massaging substance, and a massaging means. In particular the present invention is an inexpensive motor-driven hand-held massaging device, use of which guarantees a more effective massaging action and convenient handling of massaging substances. The device includes a hand-held massaging device with a plurality of rotating massaging brushes and the massaging substance is able to be fed to the individual massaging brushes at controllable intervals.

BACKGROUND OF THE INVENTION

Motor-driven hand-held massaging devices have been generally known and are used for cosmetic purposes and in medicine, e.g., for the treatment of rheumatic diseases.

Document GB 1 480 265 describes a device for massaging the skin, which consists essentially of an electromagnetic vibrating drive for oscillatingly moving a circular massaging brush, a storage container for a massaging substance, such as oil or pasty substances, and a housing with a grip.

By manually actuating an elastic storage container during the massage, a massaging substance is fed via a line to the massaging brush, which is formed by elastic naps. The massaging substance is rubbed into the skin by the vibrating movement of the massaging brush.

The separately necessary manual handling of the massaging substance and the difficulties in accurately positioning and metering the massaging substance are disadvantageous here. The use of naps and their vibrating movement, which fail to have optimal massaging action, are disadvantageous as well.

DE 43 06 242 A1 describes a device for body massage, in which a rotor massaging brush is driven by the water pressure on a shower hose. A massaging substance can be manually added to the rotor brush from a storage container. In addition to the disadvantage of having to separately, manually add a massaging substance, the limited possibility of application in a bathtub or shower stall is especially disadvantageous here.

DE 93 01 028.1 discloses a massaging device with a plurality of massaging elements fastened to a housing. The lack of feed of massaging substances to the massaging elements is especially disadvantageous here.

DE G 86 30 100.4 discloses a massaging device with a housing accommodating an electric motor and a brush-like working surface, which projects over the housing and is driven by the electric motor. The working surface is formed by a plurality of brush bodies, which originate from a support disk rotationally driven by the electric motor. The feed of massaging substances is not provided for here, either.

DE 28 30 480 A1 discloses a skin and/or hair cosmetic device, which is intended mainly for applying and introducing liquids onto/into the scalp, and which has a brush part traversed by channels, which are connected to a storage container for colored liquids via a line. The liquid is sent to the discharge openings of the channels on the bottom of the brush via a flow control valve, and it is distributed in the hair by vibration. The weak massaging action that is achieved and the awkward possibility of metering the additive are especially disadvantageous here.

SUMMARY AND OBJECTS OF THE INVENTION

The basic task of the present invention is to develop an inexpensive, motor-driven hand-held massaging device, use of which guarantees a more effective massaging action and the convenient handling of massaging substances.

The massaging device has a housing that contains an intermediate plate. A plurality of massaging brushes are arranged in a substantial circle on this intermediate plate. Each massaging brush is rotatably mounted in the intermediate plate and has a corresponding gear. Each gear engages with gears from adjacent massaging brushes, causing each massaging brush to rotate in a direction opposite to the direction of rotation of adjacent brushes. Each brush/gear unit defines an axial hole and a radial hole. The intermediate plate defines a channel or a plurality of channels which communicate with the radial hole in the brush/gear unit. The housing of the massaging device contains a storage chamber, and a pump means transfers fluid from the storage chamber to the channel in the intermediate plate. The radial holes in the brush/gear unit are angularly positioned with respect to each other and the channel or plurality of channels so that fluid enters the radial holes of each brush/gear unit at different times. The massaging brushes are arranged such that they rotate in opposite directions in relation to one another. Since the massaging brushes create a kneading effect on the skin, an optimal massaging action is guaranteed which may be additionally influenced by the automatic feed of massaging substances. The feeding of massaging substances may be turned on and off as desired. By feeding the massaging substance to one brush after the other at controllable intervals, the positioning and the metering of the massaging substance can be performed with high accuracy. The replacement of the brushes and their cleaning are simple and unproblematic. As a result, it is also possible to perform both cosmetic and medical treatments with different massaging substances using the same device.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DETAILED DESCRIPTION OF THE PREFERRED EMBODIMENT

Figure 1:
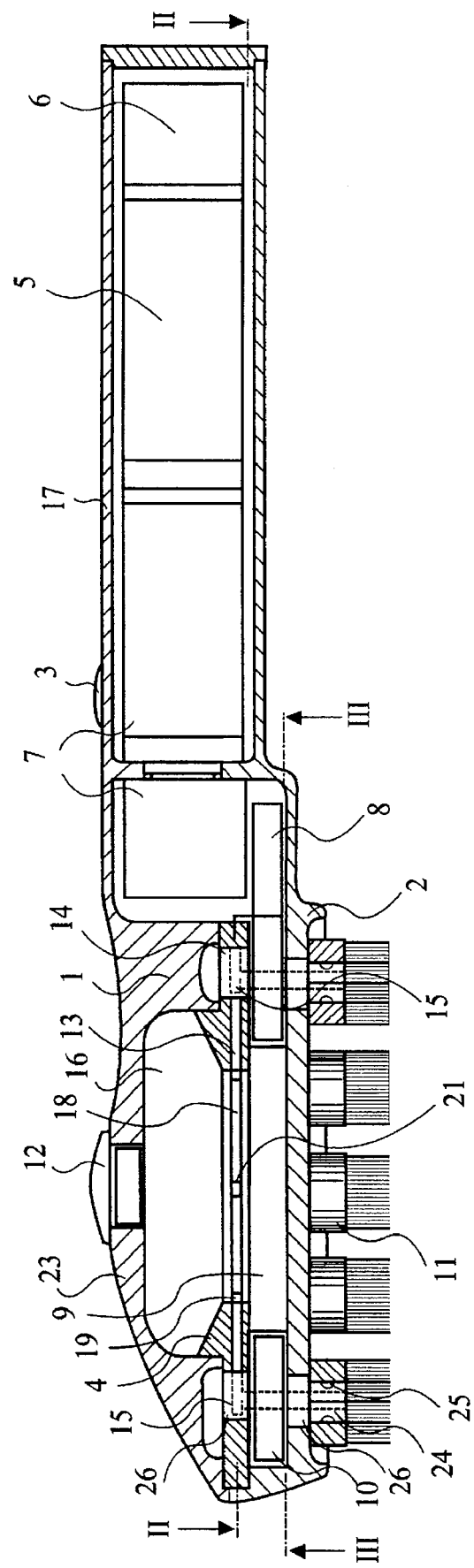
FIG. 1 is an axial longitudinal section.

FIG. 1 shows an axial longitudinal section of the essential assembly units of the hand-held massaging device. According to this figure, the hand-held massaging device consists of a housing, which is formed by an upper 1 and a lower part 2. A grip part 17 contains a motor 5 with a battery 6, a gear mechanism 7 and a driving gear 8. A fluid delivery means including a circular disk-shaped oil pump 9 and a storage chamber 16 are arranged above the grip 17 for massaging substances. Radially around the oil pump 9, there are twelve gears 10 accommodated in the head part 23. Two pushbuttons 3 for turning the motor 5 and the oil pump 9 on and off are provided on the jacket surface of the grip part 17. A closing screw 12 for the oil storage chamber 16 is provided on the head part 23. The front side of the grip part 17 contains a plug-and-socket connection, not shown, via which a power cable for charging the battery or for directly driving the motor 5 can be connected. An intermediate plate 4, in which the gears 10 are mounted, is arranged in the head part 23 of the housing between the upper part and the lower part 1, 2. Massaging brushes 11 are arranged on the underside of the gears 10.

Figure 2:
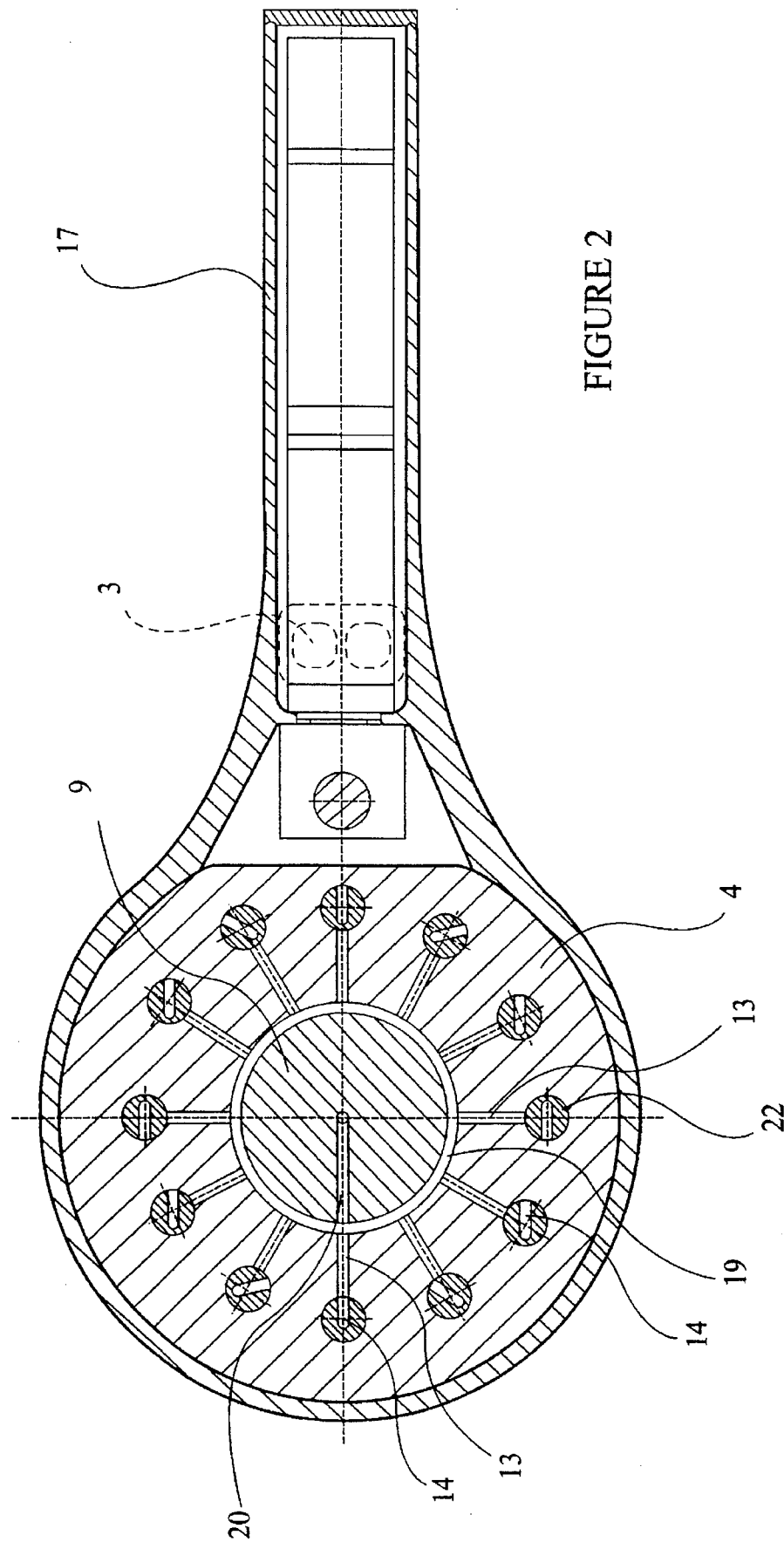
FIG. 2 is a longitudinal section according to FIG. 1 along line II—II.

According to the sectional view in FIG. 2, the intermediate plate 4 has radial holes 13, which are arranged in a star-shaped pattern. The radial holes lead from the center of the intermediate plate 4 to the mounting points 22 of the gears 10, and are used to feed oil to the brushes 11 mounted on the gears 10. The gears 10 are rotatably mounted with their press fits 26 in the intermediate plate 4 and in the housing lower part 2 (FIG. 1).

Figure 3:
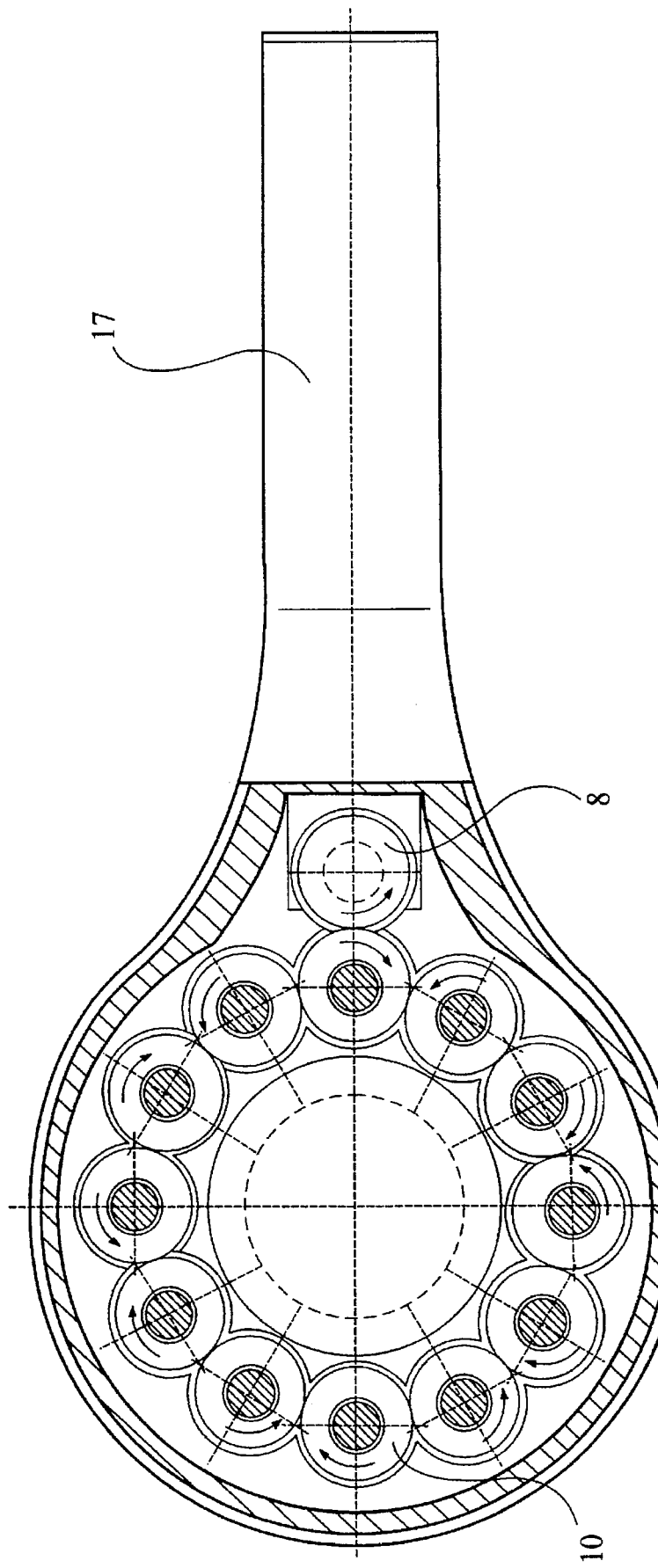
FIG. 3 shows a partial longitudinal section according to FIG. 1 along line III—III.

As is shown in FIG. 3, the gears 10 are arranged on a common pitch circle and engage the corresponding next gear 10 following them. The drive is via the driving gear 8, which is rigidly connected to the gear mechanism 7 driven by the motor 5 (FIGS. 1 and 2). The direction of rotation of the gears 10 engaging each other is alternatingly opposite, as is indicated by the arrows in FIG. 3.

As is shown in FIG. 1, the gears 10 are provided on the underside of the housing with a square 24 and an annular groove 25, which guarantee the axial and radial mounting of the brushes. The gears 10 are provided with radial blind holes 14 and with holes 15 connected to the blind holes 14, via which the oil is delivered to the brushes 11. The position of the gears 10 in relation to one another is selected to be such that only one brush 11 is supplied with oil at any one time. This is achieved by the different radial hole arrangements 14 in the gears 10 (FIG. 2). The oil pump 9, whose intake opening 21 opens into the oil storage chamber 16, is arranged in the center of the intermediate plate 4 (FIG. 1). A circular ring channel 19 on the pump flange 18 supplies the brushes 11 via the transverse holes 13 of the intermediate plate 4 (FIGS. 1 and 2).

The mode, of operation of the hand-held massaging device is described below.

The massaging brushes 11 are driven via the drive unit consisting of the motor 5, the gear mechanism 7, the driving gear 8, and the gears 10. The driving power of the motor 5 is transmitted as a rotary movement via the gear mechanism 7, which is rigidly connected to the driving gear 8, to the gears 10 with the brushes 11 mounted on them. The motor 5 is operated directly via a power cable or a battery 6. The motor 5 is turned on and off via the operating button 3 on the jacket surface of the grip part 17 (FIG. 1). The brushes 11 are moved in opposite directions of rotation relative to one another by the gears 10 arranged on a common pitch circle according to FIG. 3, which brings about a kneading action on the skin area being massaged.

The miniature oil pump 9 draws in the oil from the storage chamber 16 via the intake opening 21, and it distributes it among the holes 14, 15 in the gears 10 and among the brushes 11 (FIGS. 1 and 2) via a ring channel pump outlet 20 and the ring channel 19, as well as via the holes 13 of the intermediate plate 4. The oil pump 9 is turned on via the operating button 3 as needed. The storage chamber 16 contains approx. 50 mL of massaging oil. To achieve a uniform metering of oil at the individual brushes 11, the radial holes 14 of the gears 10 are arranged offset in relation to one another. Only one gear hole 14 coincides with the hole 13 of the intermediate plate 4 at any one time, and all other blind holes 14 are closed (FIG. 2). All gears 10 and brushes 11 are supplied with oil during each revolution of the gear mechanism.

Easy replacement of the brushes 11 is guaranteed by the square connection with the gears, which is secured against rotation. The brush 11 and the gear 10 are always fixed axially via a snap-in mechanism (FIG. 1).

The grip 17 of the housing may be designed due to an attached or screwed-on grip extension, not shown, such that all body parts can be reached with the massaging device.

While specific embodiments of the invention have been shown and described in detail to illustrate the application of the principles of the invention, it will be understood that the invention may be embodied otherwise without departing from such principles.

What is claimed is:

1. A massaging device comprising:

a housing;

a storage chamber positioned in said housing and for accommodating fluid;

a plurality of rotating massaging brushes rotatably connected to said housing;

fluid delivery means positioned in said housing and for separately delivering fluid from said storage chamber to each of said plurality of rotating massaging brushes at different times.

2. A device in accordance with claim 1, wherein:

said plurality of massaging brushes are connected to said housing by respective gears;

each of said plurality of massaging brushes including a respective gear to form a brush/gear unit;

said fluid delivery means includes an axial and radial hole in each of said brush/gear units, said fluid delivery means including an intermediate plate defining a channel to said each brush/gear unit and in communication with said radial hole at a predetermined angular position of said brush/gear unit, said fluid delivery means including pump means for transferring fluid from said storage chamber to said channel.

3. A device in accordance with claim 1, wherein:

said fluid delivery means delivers said fluid at regular repetitive intervals.

4. A device in accordance with claim 1, wherein:

said fluid delivery means periodically blocks and flows the fluid to said each brush.

5. A device in accordance with claim 1, wherein:

said fluid delivery means only delivers the fluid from said storage chamber to said plurality of brushes.

6. A device in accordance with claim 1, wherein:

said fluid delivery means delivers the fluid from said storage chamber to said plurality of brushes without diluting the fluid.

7. A device in accordance with claim 1, wherein:

said fluid delivery means delivers the fluid axially to a center of said each brush and then delivers the fluid radially outward from said center of said each brush.

8. A device in accordance with claim 1, wherein:

said plurality of massaging brushes are connected to said housing by respective gears;

each of said gears engages with adjacent said gears for rotation in a direction opposite said adjacent gears.

9. A massaging device comprising:

a housing;

a grip attached to said housing;

a storage chamber positioned in said housing and for accommodating fluid;

a plurality of rotating massaging brushes rotatably connected to said housing;

fluid delivery means positioned in said housing and for separately delivering fluid from said storage chamber to each of said plurality of rotating massaging brushes at different times.

10. A device in accordance with claim 1, wherein:

said plurality of massaging brushes are positioned substantially in a circle, means for rotating each of said plurality of massaging brushes in a direction opposite to a direction of rotation of adjacent said massaging brushes.

11. A device in accordance with claim 1, wherein:

said plurality of massaging brushes are positioned substantially in a circle, each of said plurality of massaging brushes rotating in a direction opposite to a direction of rotation of adjacent said massaging brushes.

12. A device in accordance with claim 1, wherein:

said plurality of massaging brushes are connected to said housing by respective gears;

said fluid delivery means includes an axial and radial hole in each of said respective gears, said fluid delivery means including an intermediate plate defining a plurality of channels to said each massaging brush, said plurality of channels forming a star-shaped pattern on said intermediate plate, each of said plurality of channels corresponding with said radial hole in different said massaging brushes with said respective gear, said fluid delivery means including pump means for transferring fluid from said storage chamber to said plurality of channels.

13. A device in accordance with claim 2, wherein:

said plurality of massaging brushes are connected to said housing by respective gears;

said fluid delivery means includes an axial and radial hole in each combination of said massaging brushes with said respective gear, said fluid delivery means including an intermediate plate defining a plurality of channels, said plurality of channels forming a star-shaped pattern on said intermediate plate, each of said plurality of channels corresponding with said radial hole in a different one of said massaging brushes with said respective gear, said fluid delivery means including pump means for transferring fluid from said storage chamber to said plurality of channels.

14. A device in accordance with claim 11, wherein:

said plurality of massaging brushes are connected to said housing by respective gears;

said fluid delivery means includes an axial and radial hole in each arrangement of said massaging brush with said respective gear, said fluid delivery means including an intermediate plate defining a plurality of channels to said each massaging brush, said plurality of channels forming a star-shaped pattern on said intermediate plate, each of said plurality of channels corresponding with said radial hole in different said massaging brushes with said respective gear, said fluid delivery means including pump means for transferring fluid from said storage chamber to said plurality of channels.

15. A device in accordance with claim 12, wherein:

said radial holes are angularly positioned with respect to each other and said channels to correspond with a respective one of said channels at different times.

16. A device in accordance with claim 12, wherein:

said plurality of massaging brushes are positioned substantially in a circle;

said pump means is positioned in said intermediate plate and substantially in a center of said circle of said massaging brushes, an intake opening of said pump means opens into said storage chamber;

said intermediate plate defines a ring channel in communication with said plurality of channels, a pump flange of said pump means is in communication with said circular channel.

17. A device in accordance with claim 12, wherein:

said housing includes a first part and a second part, said intermediate plate being positioned between said first and second parts;

said gears are rotatably mounted in said intermediate plate and said second part in a substantially circular pattern, each of said gears engage an adjacent said gear, said gears being driven by an electric motor in said grip via a drive gear.

18. A device in accordance with claim 1, wherein:

said brushes are designed to be repetitively replaceable.

* * * * *